United States Patent [19]

Káldor et al.

[11] Patent Number: 4,656,290

[45] Date of Patent: Apr. 7, 1987

[54] PROCESS FOR PREPARING THIO, DITHIO OR CARBONYL COMPOUNDS

[75] Inventors: István Káldor, Göd; András Szász, Budapest; Ilona Vegh, Budapest; József Heizer, Budapest; Eva Benedek, Budapest, all of Hungary

[73] Assignee: Chinoin Gyogyszer es Vegyeszeti Termekek Gyara Rt., Budapest, Hungary

[21] Appl. No.: 691,972

[22] Filed: Jan. 16, 1985

[30] Foreign Application Priority Data

Nov. 27, 1984 [HU] Hungary .................. 154/84

[51] Int. Cl.$^4$ .......................... C07D 235/32
[52] U.S. Cl. ..................... 548/306; 544/182;
544/215; 544/219; 544/237; 544/238; 544/295;
544/296; 544/353; 544/354; 544/355; 544/359;
546/140; 546/168; 546/178; 546/255; 546/262;
548/328; 548/336; 548/455; 548/518
[58] Field of Search ............... 548/306, 328, 336, 455,
548/518; 546/140, 168, 178, 255, 262; 544/182,
215, 219, 237, 238, 295, 296, 353, 354, 355, 359

[56] References Cited

PUBLICATIONS

*Chemical Abstracts,* 101:6812s (1984) [Japan Kokai 5942,362, 3/8/84].
Johnson, C. et al., *J. Org. Chem.,* 37(6), 919–920 (1972).
*Chemical Abstracts,* 88:191379e (1978) [Houghten, R. et al., *Pept., Proc. Am. Pept. Symp.,* 5th 1977, 458–60].
*Chemical Abstracts,* 71:70027d (1969) [Russell, G. et al., *J. Org. Chem.,* 1969, 34(8), 2336–9].
*Chemical Abstracts,* 89:108478p (1978) [Drabowicz, J. et al., *Synthesis* 1978, (7), 542].
Nakagawa, K. et al., *Tetrahedron Letters,* No. 5, pp. 343–346, 1972.

Borgogno, G. et al., *Synthesis,* pp. 529–531 (1975).

*Primary Examiner*—Richard A. Schwartz
*Attorney, Agent, or Firm*—Karl F. Ross; Herbert Dubno

[57] ABSTRACT

A process is disclosed for the preparation of compounds of the Formula I $$R-X-R^1 \tag{I}$$

wherein X is thio, dithio or carbonyl and R and $R^1$ are defined hereinbelow which comprises reducing a compound of the Formula II $$R-A \tag{II}$$

wherein A is chlorosulfonyl or a group of the Formula $$-\overset{O}{\underset{\|}{C}}-R^1 \quad \text{or} \quad -\overset{O}{\underset{\|}{\overset{\uparrow}{S}}}-R^1$$

with a sulfur compound comprising sulfur which is of the (+)4 oxidation degree and is converted into the (+)6 oxidation degree during the process or with a sulfur compound which is decomposed in acidic medium to a compound of the latter oxidation degree in the presence of a catalytic amount but not more than 0.5 mole—related to 1 mole of the starting material of the Formula II—of elemental iodine or a compound capable of delivering hydrogen iodide in acidic medium or a compound which can be reduced to hydrogen iodide in acidic medium with the sulfur compound used.

21 Claims, No Drawings

PROCESS FOR PREPARING THIO, DITHIO OR CARBONYL COMPOUNDS

SPECIFICATION

This invention relates to a new process for the preparation of compounds of the formula I

by reducing sulfonic acid chlorides, sulfoxides or halogeno derivatives of the formula II

In the prior art several methods are known for the reduction of sulfonic acid chlorides into disulfides. Benzene sulfonyl chloride may be transformed into phenyl disulfide in ethereal solution by treating same with an equimolar amount of lithium aluminum hydride [J. Org. Chem. 1951, (16) page 946]. The 3-nitro-benzene sulfonic acid chloride may be reduced to 3-nitro-phenyl-disulfide with concentrated hydrogen iodide [Org. Synth. Coll. Vol. 5, (1973)]. Benzene sulfonic acid chloride may be converted into phenyl-disulfide in an aqueous-acetic acid medium in the presence of red phosphorous and a catalytic amount of iodine [C.A. 52, 2791 (1958)].

It is known that the reduction of sulfoxides may be carried out i.e. with tin(II)chloride (Synthesis 1973 page 206), hydrogen in the presence of a palladium-charcoal catalyst (Synthesis 1975 page 385), sodium borohydride in the presence of cobalt(II)chloride [J. Org. Chem. 19, (46) p. 613]or hydrogen iodide (Z. Obs. Khim. 29, 3033=C.A. 54 12096 d).

The above processes are accompanied by several drawbacks: the yields are often poor, the selectivity is low; the methods are suitable only for the preparation of a narrow compound group; in order to obtain a satisfactory yield often an extremely long reaction time is required; the reactants and reaction conditions are unsuitable for industrial scale production.

We have studied the possibilities of the reduction of 2-[(methoxycarbonyl)-amino]-1H-benzimidazole-5-sulfonic acid chloride—described in U.S. Pat. No. 4,368,328 the first time—into 5,5'-(2-carbomethoxyamino-benzimidazole)-yl-disulfide. The above two compounds are useful intermediates in the preparation of the excellent anthelmintic agent "Albendazol" [2-(methoxycarbonyl)amino-5-propylthio-1H-benzimidazole; DOS No. 2,820,375].

According to the present invention there is provided a new reduction system which is highly suitable for the selective reduction of not only the above sulfonic acid chloride but also for the selective reduction of a large number of other sulfonic acid chlorides, sulfoxides and halogeno compounds.

The basic of the present invention resides in the use of the said new reduction system for the preparation of both new and known compounds.

According to the present invention there is provided a process for the preparation of compounds of the formula (I)

R—X—R¹ (I)

wherein
X is thio, dithio or carbonyl;

R and R¹ represent independently of each other hydrogen, hydroxy; or straight or branched chain $C_{1-12}$ alkyl or $C_{2-12}$ alkenyl optionally bearing one or more hydroxy, carboxy, $C_{1-6}$ alkoxycarbonyl, amino, acetylamino, nitro, $C_{1-6}$ alkylamino, $C_{1-6}$ alkoxy,

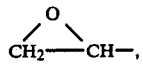

$C_{5-7}$ cycloalkyl optionally substituted by one or more hydroxy groups and/or halogeno substituents; $C_{7-10}$ aralkyl; phenyl or naphthyl optionally bearing one or more $C_{1-4}$ alkyl, nitro and/or halogeno substituents; a 5- or 6-membered heterocycle containing 1-3 nitrogen atoms, optionally fused with a benzene ring and optionally bearing one or more identical or different substituents, preferably 2-carbomethoxyamino-1H-benzimidazole-5-yl, pyrrolyl, indolyl, imidazolyl, benzimidazolyl, pyridyl, quinolyl, isoquinolyl, 1,2-, 1,3- or 1,4-diazinyl, 1,2,4- or 1,3,5-triazinyl, phthalazinyl or quinoxalyl; α-halogeno-substituted $C_{7-10}$ aralkyl or a group of the formula —$(CH_2)_n$—Hal wherein n is 1-6 which comprises reducing a compound of the formula II

R—A (II)

wherein A is chlorosulfonyl or a group of the formula

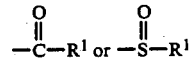

and R¹ and R are stated above with a sulfur compound comprising sulfur which is of the (+)4 oxidation degree and is converted into the (+)6 oxidation degree during the process or with a sulfur compound which is decomposed in acidic medium to a compound of the latter oxidation degree preferably in the presence of a catalytic amount but not more than 0.5 mole—related to 1 mole of the starting material of the formula II—of elemental iodine or a compound capable of delivering hydrogen iodide in acidic medium or a compound which can be reduced to hydrogen iodide in acidic medium with the sulfur compound used; and if desired alkylating the compound of the formula I thus obtained wherein R is as stated above; R¹ stands for hydrogen and X is dithio group optionally in the presence of cyanide ions with a compound of the formula R¹-Halogen (wherein R¹ is $C_{1-3}$ alkyl and halogen represents bromine or chlorine) by methods known per se.

A preferred feature of the invention is a process directed to preparing a compound of the formula (Ia)

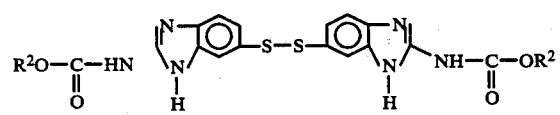

wherein $R^2$ is $C_1$-$C_3$ alkyl, which comprises the step of reducing a compound of the formula (II)

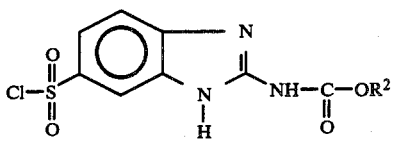

with a sulfur compound comprising sulfur having an oxidation number of (+4) and which is converted into a sulfur compound having an oxidation number of (+6) during the process or with a sulfur compound which is decomposed in an acidic medium to a compound of the latter oxidation state, preferably in the presence of a catalytic amount, but not more than 0.5 moles relative to 1 mole of the compound of the formula (IIa) of elemental iodine or a compound capable of delivering hydrogen iodide in acidic medium with the sulfur compound used.

The compounds of the formula (Ia) are especially useful as intermediates in the preparation of "Albendazol" and are related compounds. See DOS No. 2,820,375.

The reaction may be carried out at a temperature between 10° C. and 150° C., particularly at 40°-60° C. As reaction medium inert solvents or mixtures thereof, advantageously a mineral or organic acid comprising 1–50% of weight by water, or a mixture thereof may be used. As organic solvent preferably acetic acid, formic acid or propionic acid and as mineral acid preferably sulfuric acid, phosphoric acid or hydrochloric acid may be used.

As sulfur compound of (+)4 oxidation degree preferably sulfur dioxide, an alkali metal or alkaline earth metal sulfite, hydrogen sulfite (bisulfite) or thiosulfate may be used. As agent reducible to hydrogen iodide in acidic medium preferably an alkali metal iodide may be used.

The starting materials of the formula (II) are known commercial products and may be partly prepared by methods known per se and generally used in organic chemistry (J. Chem. Soc. Co. 1981, (6) page 295). The preparation of 2-carbomethoxyamino-1H-benzimidazole-5-sulfonyl chloride is described in Example 1 of U.S. Pat. No. 4,368,328.

The compounds of the formula I exhibit valuable stimulant effect (DOS No. 3,243,352).

The following compounds of the formula I disclosed in the said DOS and obtainable by the process of the present invention possess particularly valuable stimulant properties:

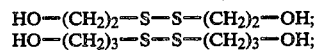  (a)
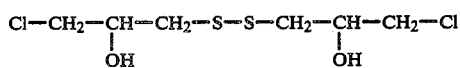  (b)

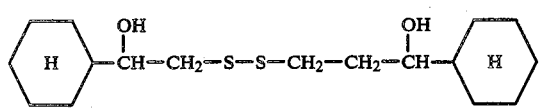  (c)

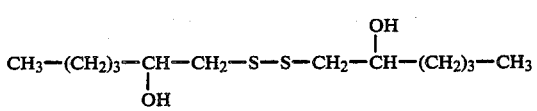  (d)

(e)

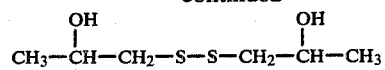  (f)

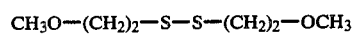  (g)

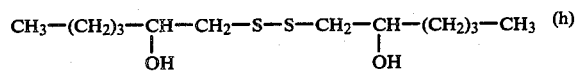  (h)

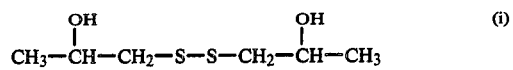  (i)

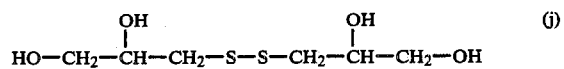  (j)

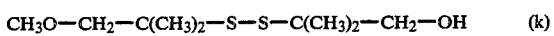  (k)

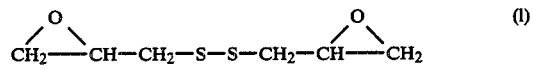  (l)

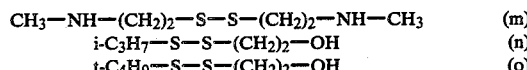  (m)
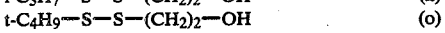  (n)
  (o)

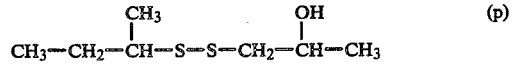  (p)

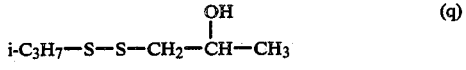  (q)

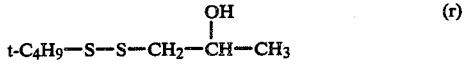  (r)

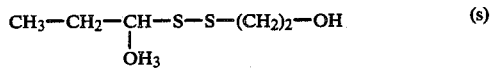  (s)

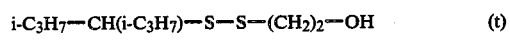  (t)

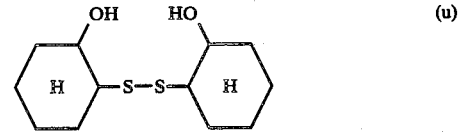  (u)

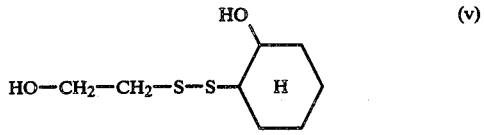  (v)

The new reduction method of the present invention has the following advantages:

According to this process symmetrical and mixed thioethers and disulfides can be prepared from sulfides and sulfonic acids, respectively and a halogeno atom adjacent to an aldehyde or keto carbonyl group, respectively can be replaced by hydrogen.

The process is highly selective and can be applied e.g. in the presence of an alcoholic hydroxy, aldehyde-, ketone- or ester-carbonyl, carboxylic acid and nitro group and optionally activated double bonds.

Further details of the present invention are to be found in the following Examples without limiting the scope of protection to the said Examples.

EXAMPLE 1

Preparation of p-tolyl-disulfide 19 g (0.1 mole) of p-toluene sulfonyl chloride are dissolved in 100 ml acetic acid whereupon 1.5 g (0.01 mole) of sodium iodide are added and the reaction mixture is stirred until the iodide is completely dissolved (5 minutes). The reaction mixture becomes dark brown. A 30% sodium bisulfite solution is slowly added dropwise at a rate that on addition the iodine color of the mixture should just disappear. During the dropwise addition the temperature of the mixture is raised to 60° C. (within about 30 minutes). The reaction is continued at this temperature until the color of iodine does not appear any more. At the end of the reaction the reaction mixture is diluted with 50 ml of water and the pH is adjusted to the value of 4 by adding a 20% sodium hydroxide solution. The reaction mixture is extracted three times with 80 ml of n-hexane each, the hexane phases are combined, dried over anhydrous sodium sulfate and evaporated under atmospheric pressure. From the distillation residue the traces of solvent are removed at 70° C. in vacuo and the product is crystallized at 20° C. Thus 11.9 g of p-tolyl-disulfide are obtained, yield 97%. Mp.: 43°–45° C.

$^1$H-NMR: (CDCl$_3$): aromatic 7.35 ppm (d) 2H, 7.05 ppm (d) 2H, CH$_3$ 2.8 ppm (s) 3H.

EXAMPLE 2

Preparation of phenyl-disulfide

One proceeds according to Example 1 except that p-toluene sulfonyl chloride is replaced by benzene sulfonyl chloride as starting material. Thus 10 g of phenyl-disulfide are obtained, yield 93%. Mp.: 58°–60° C.

$^1$H-NMR: (CDCl$_3$) aromatic 7.6–7.0 ppm (m).

EXAMPLE 3

Preparation of methyl disulfide

One proceeds according to Example 1 but p-toluene sulfonyl chloride is replaced by the methane sulfonyl chloride as starting material. On working up the reaction mixture the pH is adjusted to 8 instead of the value of 4 and the reaction mixture is extracted three times with 50 ml of ether each. The ethereal extracts are united, dried and fractionated. Thus 2.85 g of methyl disulfide are obtained, yield 61% Bp: 107°–109° C., $n_D^{25}=1.5249$.

EXAMPLE 4

Preparation of 5,5′-(2-carbomethoxyamino-benzimidazole)-yl-disulfide

One proceeds according to Example 1 but as starting material p-toluene sulfonyl chloride is replaced by 2-carbomethoxyamino-benzimidazole-5-sulfonyl chloride and on working up the reaction mixture the hexane extraction step is omitted and the reaction mixture adjusted to the pH value of 4 is filtered at 50° C. and the crystals are washed sulfate-ion free with three times with 10 ml hot water each. The product is dried in vacuo at 100° C. Thus 18.2 g of the desired compound are obtained, yield 82%.

M.p.: 323°–325° C.

$^1$H-NMR (TFA-d$_1$): C$_7$—H 7.8 ppm s 1H, C$_6$—H 7.6 ppm s 2H, C$_4$—H 7.6 ppm s 2H, OCH$_3$ 4.0 ppm s 3H.

EXAMPLE 5

Preparation of 2-[(methoxycarbonyl)-amino]-5-propylthio-1H-benzimidazole 36 g of 5,5′-(2-carbomethoxyamino-benzimidazole)-yl-disulfide prepared according to Example 4 are dissolved in a mixture of 30 g of potassium hydroxide, 25 ml of propyl bromide, 7 g of potassium cyanide, 250 ml of water and 500 ml of acetone. The reaction mixture is stirred at 20°–25° C. for 20 hours, whereupon 35 g of sodium hydrogen carbonate are added. The precipitated product is filtered off and washed with 200 ml of 50 vol% of aqueous acetone and 200 ml of water. Thus 33 g of the desired compound are obtained, yield 75%. Mp.: 210°–212° C.

EXAMPLE 6

Preparation of p-tolyl-cis-trans-1-propenyl-thioether 10 millimoles of p-tolyl-cis-trans-1-propenyl-sulfoxide are dissolved in 10 ml of acetic acid and 0.2 g of sodium iodide are added. The temperature of the mixture is raised to 50° C. and the reaction is started by adding 2 drops of concentrated hydrochloric acid. The iodine formed is reduced by continuous addition of a 30% sodium bisulfite solution, whereupon after disappearance of the color of iodine 3–5 drops of concentrated hydrochloric acid are added. The concentrated hydrochloric acid and sodium bisulfite solution are alternatively added until on further addition of hydrochloric acid the color of iodine does not appear any more.

The reaction mixture is diluted with 10 ml of water, the pH is adjusted to 8 and the thioether formed is extracted three times with 15 ml of n-hexane each. After extraction the hexane phases are united, dried over sodium sulfate and the solvent is removed. Thus 2.1 g of p-tolyl-cis-trans-1-propenyl-thioether are obtained as distillation residue.

EXAMPLE 7

Preparation of methyl-phenyl-thioether (thioanizole)

One proceeds according to Example 6 but methyl-phenyl-sulfoxide is substituted for p-tolyl-cis-trans-1-propenyl-sulfoxide as starting material, and the distillation residue obtained after the removal of the solvent is fractionated. Thus 1.1 g of the desired compound are obtained, yield 88%, bp.: 181° C., $n_D^{25}=1.5850$. (1 bar)

$^1$NMR (CDCl$_3$) aromatic 7.4 ppm (s) 5H, —CH$_3$ 2.47 ppm (s) 3H.

EXAMPLE 8

Preparation of p-tolyl-n-propyl-thioether

One proceeds according to Example 6 except that n-propyl-p-tolyl-sulfoxide is used as starting material and the distillation residue obtained after the removal of the solvent is fractionated. Thus 1.4 g of the desired compound are obtained, yield 92%. Bp.: 78°–80° C. (266 Pa), $n_D^{25}=1.5450$.

$^1$H-NMR (CDCl$_3$) aromatic 7.25 ppm (d) 2H, 7.05 ppm (d) 2H, SCH$_2$ 2.85 ppm (t) 2H, CH$_3$ 2.3 ppm (s) 3H, CH$_2$CH$_3$ 1.65 ppm (m) 2H, CH$_2$CH$_3$ 1.0 ppm (t) 3H.

EXAMPLE 9

Preparation of p-tolyl-allyl-thioether

One proceeds according to Example 6 except that p-tolyl-allyl-sulfoxide is used as starting material. Thus 0.65 g of the desired compound are obtained, yield 39%. Bp.: 70°–73° C. (266 Pa), $n_D^{25} = 1.5710$.

$^1$H-NMR (CDCl$_3$): aromatic 7.25 ppm (d) 2H, 7.05 ppm (d) 2H, —CH= 6.1–5.6 ppm (m) $^{3J}$CH, =CH$_A$=1, $^{3J}$CH=CH$_B$, =CH$_2$ 5.1 ppm (dd) 2H$^{2J}$CH$_A$=CH, SCH$_2$ 3.5 ppm (d) 2H$^{3J}$CH$_2$, CH= 6m8, $^{4J}$CH$_2$, =CH$_2$=0.8, —CH$_3$ 2.3 ppm (s) 3H.

EXAMPLE 10

Preparation of phenyl-3-butenyl-thioether

One proceeds according to Example 6 except that phenyl-3-butenyl-sulfoxide is used as starting material. Thus 1.2 g of the desired compound are obtained, yield 72%.

$^1$H-NMR (CDCl$_3$) aromatic 7.5–7.0 ppm (m) 5H, —CH= 6.15–5.6 ppm (m) 1H, =CH$_2$ 5.1 ppm (dd) 2H, —SCH$_2$ 3.0 ppm (t) 2H$^{3J}$CH$_2$, CH$_2$=8, —CH$_2$CH= 2.85 ppm (q) 2H.

EXAMPLE 11

Preparation of p-tolyl-benzyl thioether

One proceeds according to Example 6 except that p-tolyl-benzyl-sulfoxide is used as starting material. Thus 1.9 g of the desired compound are obtained, yield 88.7%, mp.: 43°–44° C.

$^1$H-NMR (CDCl$_3$): monosubst. aromatic 7.25 ppm (s) 5H, disubst. aromatic 7.1 ppm (dd) 4H, —CH$_2$— 4.05 ppm (s) 2H, —CH$_3$ 2.3 ppm (s) 3H.

EXAMPLE 12

Preparation of phenyl-β-phenylethyl-thioether

One proceeds according to Example 6 except that phenyl-β-phenylethyl-sulfoxide is used as starting material. Thus 1.6 g of the desired compound are obtained, yield 75%, $n_D^{25} = 1.6101$.

$^1$H-NMR (CDCl$_3$): aromatic 7.25–7.0 ppm (m) 10H, —CH$_2$CH$_2$ 3.0 ppm (m) 4H.

EXAMPLE 13

Preparation of n-propyl-5-(2-carbomethoxyamino-benzimidazole)-yl-thioether

One proceeds according to Example 6 except that n-propyl-5-(2-carbomethoxyamino-benzimidazole)-yl-sulfoxide is used as starting material. On working up the reaction mixture the hexane extraction is omitted and the reaction mixture is neutralized (pH 7), the precipitated crystals are filtered off and washed three times with 10 ml of water each. Thus 2.1 of the desired compound are obtained, yield 79%, mp.: 210°–212° C.

1H-NMR (DMSO): —NH 11.6 ppm (s) 1H, C$_7$—H 7.45 ppm (s) 1H, C$_7$—H 7.35 ppm (d) 1H, C$_6$—H 7.1 ppm (d) 1H, O—CH$_3$ 3.75 ppm (s) 3H, S—CH$_2$ 2.75 ppm (t) 2H, —CH$_2$CH$_3$ 1.55 ppm (m) 2H.

EXAMPLE 14

Preparation of phenyl acetaldehyde 100 millimoles of α-bromo-α-phenyl-acetaldehyde are dissolved in 100 ml of acetic acid. To the solution 0.3 g (2 millimoles) of sodium iodide are added and the mixture is stirred until the iodide is completely dissolved. The iodine formed in the reaction is continuously reduced by adding a 30% potassium bisulfite solution (bisulfite consumption 4.5 ml). When no more iodine is formed the pH is adjusted to 4 by adding a 10% sodium hydroxide solution. The reaction mixture is extracted three times with 20 ml of ether each, the ethereal phases are united, dried over sodium sulfate and the ether is distilled off. The residue is fractionated in vacuo. Thus 4.5 g of the desired compound are obtained, yield 38%. Bp.: 108° C. (660 Pa). $^1$H-NMR (CDCl$_3$): CHO 9.75 ppm (t) 1H, aromatic 7.5–7.0 ppm (m) 5H, —CH$_2$— 3.65 ppm (d) 2H$^{3J}$CH$_2$ CHO=, =2.3 Hz.

EXAMPLE 15

Preparation of p-nitro-acetophenone

One proceeds according to Example 14 but bromo-methyl-p-nitro-phenyl-ketone is used as starting material in the place of α-bromo-α-phenyl-acetaldehyde. The reaction mixture is not worked up by the extraction method according to Example 14 but by precipitating the product with 50 ml of water, filtering off the same and washing it three times with 20 ml of water each. Thus 16.1 g of the desired compound are obtained, yield 98%.

M.p.: 78°–79° C.

$^1$H-NMR (CDCl$_3$) aromatic 8.3 ppm (d) 2H, 8.1 ppm (d) 2H, —CH$_3$ 2.6 ppm (s) 3H.

EXAMPLE 16

Preparation of p-tolyl-5-(2-carbomethoxyamino-1H-benzimidazole)-yl-disulfide 1.9 g (10 millimoles) of p-toluene-sulfonyl chloride and 2.9 g (10 millimoles) of 2-[(methoxycarbonyl)-amino]-1H-benzimidazole-5-sulfonyl chloride are dissolved in 20 ml of acetic acid. To the solution 0.3 g (2 millimoles) of sodium iodide are added and the mixture is stirred until the iodide is dissolved. The solution gets a dark iodine color. The iodine formed in the reaction is continuously reduced by adding a 30% sodium bisulfite solution. The temperature of the reaction mixture is gradually raised in the mean time to 70° C. within 30 minutes. At the end of the reaction the color of iodine does not appear any more. The sodium bisulfite solution consumption amounts to 20 ml. The pH of the reaction mixture is adjusted to 4 by adding a 20% sodium hydroxide solution, the precipitated crystals are filtered off and washed three times with 20 ml of water each. The product is subjected to chromatography on a Kieselgel G (Stahl) column (length: 25 cm; diameter: 2.5 cm) under an overpressure of 2 bar and diluted with a 9:1 mixture of chloroform and acetic acid. The R$_f$ value of the desired compound is 0.62. On evaporating the eluate the desired compound is obtained with a yield of 40%.

M.p.: 225°–230° C.

$^1$H-NMR (DMSO-d$_6$) —NH— 12.65 ppm (s) 1H, aromatic 7.6–7.1 ppm (m) 7H, —O—CH$_3$— 3.75 ppm (s) 3H, —CH$_3$ 2.3 ppm (s) 3H.

We claim:

1. A process for the preparation of a compound of the Formula I

R—X—R$^1$     (I)

wherein X is dithio; R and R¹ are identical and each represents hydrogen, hydroxy; or straight or branched chain $C_{1-12}$ alkyl or $C_{2-12}$ alkenyl optionally bearing one or more hydroxy, carboxy, $C_{1-6}$ alkoxycarbonyl, amino, acetylamino, nitro, $C_{1-6}$ alkylamino, $C_{1-6}$ alkoxy,

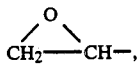

$C_{5-7}$ cycloalkyl optionally substituted by one or more hydroxy groups and/or halogeno substituents; $C_{7-10}$ aralkyl; phenyl or naphthyl optionally bearing one or more $C_{1-4}$ alkyl, nitro and/or halogeno substituents; a 5- or 6-membered heterocycle containing 1-3 nitrogen atoms, optionally fused with a benzene ring and optionally bearing one or more identical or different substituents; alpha-halogeno-substituted $C_{7-10}$ aralkyl or a group of the Formula —$(CH_2)_n$—Hal, wherein n is 1–6 which comprises reducing a compound of the Formula II $$R—A \qquad (II)$$

wherein A is chlorosulfonyl with a sulfur compound comprising sulfur which is of the (+)4 oxidation degree and is converted into the (+)6 oxidation degree during the process or with a sulfur compound which is decomposed in acidic medium to a compound of the latter oxidation degree in the presence of a catalytic amount but not more than 0.5 mole—related to 1 mole of the starting material of the Formula II—of elemental iodine or a compound capable of delivering hydrogen iodide in acidic medium or a compound which can be reduced to hydrogen iodide in acidic medium with the sulfur compound used.

2. The process defined in claim 1, which comprises carrying out the reduction in a mixture of water and a mineral acid and/or an organic acid.

3. The process defined in claim 1, which comprises using an alkali metal hydrogen sulfite, sulfite, or thiosulfate as the compound of the (+4) oxidation degree.

4. The process defined in claim 1, which comprises using an alkali metal iodide as the compound delivering hydrogen iodide in an acidic medium.

5. The process defined in claim 1, which comprises carrying out the reduction at a temperature of 10° to 150° C.

6. A process for the preparation of a compound of the Formula I $$R—X—R^1 \qquad (I)$$

wherein X is dithio; R and R¹ are each different and represent independently of each other hydrogen, hydroxy; or straight or branched chain $C_{1-12}$ alkyl or $C_{2-12}$ alkenyl optionally bearing one or more hydroxy, carboxy, $C_{1-6}$ alkoxycarbonyl, amino, acetylamino, nitro, $C_{1-6}$ alkylamino, $C_{1-6}$ alkoxy,

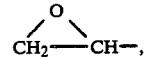

$C_{5-7}$ cycloalkyl optionally substituted by one or more hydroxy groups and/or halogeno substituents; $C_{7-10}$ aralkyl; phenyl or naphthyl optionally bearing one or more $C_{1-4}$ alkyl, nitro and/or halogeno substituents; a 5- or 6-membered heterocycle containing 1-3 nitrogen atoms, optionally fused with a benzene ring and optionally bearing one or more identical or different substituents; alpha-halogeno-substituted $C_{7-10}$ aralkyl or a group of the Formula —$(CH_2)_n$—Hal, wherein n is 1–6 which comprises reducing equimolar amounts of a compound of the Formula II $$R—A \qquad (II)$$

and a compound of the Formula (IIa)

$$R^1—A$$

wherein A is chlorosulfonyl with a sulfur compound comprising sulfur which is of the (+)4 oxidation degree and is converted into the (+)6 oxidation degree during the process or with a sulfur compound which is decomposed in acidic medium to a compound of the latter oxidation degree in the presence of a catalytic amount but not more than 0.5 mole—related to 1 mole of the starting material of the Formula II—of elemental iodine or a compound capable of delivering hydrogen iodide in acidic medium or a compound which can be reduced to hydrogen iodide in acidic medium with the sulfur compound used; and if desired alkylating the compound of the Formula I thus obtained wherein R and X are as stated above and R¹ stands for hydrogen optionally in the presence of cyanide ions with a compound of the Formula R¹-Halogen wherein R¹ is $C_{1-3}$ alkyl and Halogen represents bromine or chlorine.

7. The process defined in claim 6, which comprises carrying out the reduction in a mixture of water and a mineral acid and/or an organic acid.

8. The process defined in claim 6, which comprises using an alkali metal hydrogen sulfite, sulfite, or thiosulfate as the compound of the (+4) oxidation degree.

9. The process defined in claim 6, which comprises using an alkali metal iodide as the compound delivering hydrogen iodide in an acidic medium.

10. The process defined in claim 6, which comprises carrying out the reduction at a temperature of 10° to 150° C.

11. A process for the preparation of a compound of the Formula I $$R—X—R^1 \qquad (I)$$

wherein X is thio; R and R¹ represent independently of each other hydrogen, hydroxy; or straight or branched chain $C_{1-12}$ alkyl or $C_{2-12}$ alkenyl optionally bearing one or more hydroxy, carboxy, $C_{1-6}$ alkoxycarbonyl, amino, acetylamino, nitro, $C_{1-6}$ alkylamino, $C_{1-6}$ alkoxy,

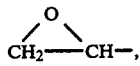

$C_{5-7}$ cycloalkyl optionally substituted by one or more hydroxy groups and/or halogeno substituents; $C_{7-10}$ aralkyl; phenyl or naphthyl optionally bearing one or more $C_{1-4}$ alkyl, nitro and/or halogeno substituents; a 5- or 6-membered heterocycle containing 1-3 nitrogen atoms, optionally fused with a benzene ring and optionally bearing one or more identical or different substituents; alpha-halogeno-substituted $C_{7-10}$ aralkyl or a group of the Formula —$(CH_2)_n$—Hal, wherein n is 1–6 which comprises reducing a compound of the Formula II

R—A   (II)

wherein A is a group of the Formula

with a sulfur compound selected from the group consisting of an alkali metal or alkaline earth metal hydrosulfite, sulfite or thiosulfate and sulfur dioxide in the presence of a catalytic amount but not more than 0.5 mole—related to 1 mole of the starting material of the Formula II—of elemental iodine or a compound capable of delivering hydrogen iodide in acidic medium or a compound which can be reduced to hydrogen iodide in acidic medium with the sulfur compound used.

12. The process defined in clam 11, which comprises carrying out the reduction in a mixture of water and a mineral acid and/or an organic acid.

13. The process defined in claim 11, which comprises using an alkali metal iodide as the compound delivering hydrogen iodide in an acidic medium.

14. The process defined in claim 11, which comprises carrying out reduction at a temperature of 10° to 150° C.

15. A process for the preparation of a compound of the Formula I

R—X—R$^1$   (I)

wherein X is carbonyl; R and R$^1$ represent independently of each other hydrogen, hydroxy; or straight or branched chain C$_{1-12}$ alkyl or C$_{2-12}$ alkenyl optionally bearing one or more hydroxy, carboxy, C$_{1-6}$ alkoxycarbonyl, amino, acetylamino, nitro, C$_{1-6}$ alkylamino, C$_{1-6}$ alkoxy,

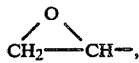

C$_{5-7}$ cycloalkyl optionally substituted by one or more hydroxy groups and/or halogeno substituents; C$_{7-10}$ aralkyl; phenyl or naphthyl optionally bearing one or more C$_{1-4}$ alkyl, nitro and/or halogeno substituents; a 5- or 6-membered heterocycle containing 1-3 nitrogen atoms, optionally fused with a benzene ring and optionally bearing one or more identical or different substituents; alpha-halogeno-substituted C$_{7-10}$ aralkyl or a group of the Formula —(CH$_2$)$_n$—Hal, wherein n is 1-6 which comprises reducing a compound of the Formula II

R—A   (II)

wherein A is a group of the Formula

wherein R and R$^1$ are as defined above except that at least one of R and R$^1$ must contain an alpha-halogen atom, with a sulfur compound comprising sulfur which is of the (+)4 oxidation degree and is converted into the (+)6 oxidation degree during the process or with a sulfur compound which is decomposed in acidic medium to a compound of the latter oxidation degree in the presence of a catalytic amount but not more than 0.5 mole—related to 1 mole of the starting material of the Formula II—of elemental iodine or a compound capable of delivering hydrogen iodide in acidic medium or a compound which can be reduced to hydrogen iodide in acidic medium with the sulfur compound used.

16. The process defined in claim 15, which comprises carrying out the reduction in a mixture of water and a mineral acid and/or an organic acid.

17. The process defined in claim 15, which comprises using an alkali metal hydrogen sulfite, sulfite, or thiosulfate as the compound of the (+4) oxidation degree.

18. The process defined in claim 15, which comprises using an alkali metal iodide as the compound delivering hydrogen iodide in an acidic medium.

19. The process defined in claim 15, which comprises carrying out the reduction at a temperature of 10° to 150° C.

20. A process for the preparation of a compound of the Formula (Ia)

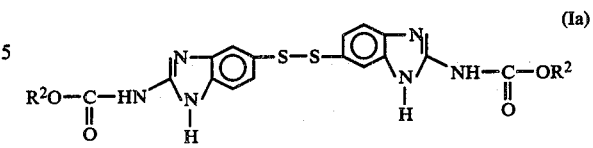

wherein R$^2$ is C$_1$–C$_3$ alkyl, which comprises the step of reducing a compound of the Formula (II)

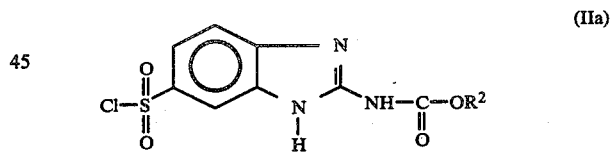

with a sulfur compound comprising sulfur having an oxidation number of +4 and which is converted into a sulfur compound having an oxidation number of +6 during the process or with a sulfur compound which is decomposed in an acidic medium to a compound of the latter oxidation state, in the presence of a catalytic amount, but not more than 0.5 moles relative to 1 mole of the compound of the Formula (II) of elemental iodine or a compound capable of delivering hydrogen iodide in acidic medium or a compound which can be reduced to hydrogen iodide in acidic medium with the sulfur compound used.

21. The process defined in claim 20 wherein the compound of the Formula (I) is 5,5'-(2-carbomethoxyaminobenzimidazole)-yl-disulfide.

* * * * *